United States Patent
Plews

Patent Number: 5,755,681
Date of Patent: May 26, 1998

[54] ADHESIVE MATERIAL WITH REMOVABLE CARRIER

[75] Inventor: Jacqueline Plews, Cottingham, United Kingdom

[73] Assignee: Smith & Nephew PLC, London, United Kingdom

[21] Appl. No.: 687,345

[22] PCT Filed: Feb. 2, 1995

[86] PCT No.: PCT/GB95/00210

§ 371 Date: Nov. 7, 1996

§ 102(e) Date: Nov. 7, 1996

[87] PCT Pub. No.: WO95/20929

PCT Pub. Date: Aug. 10, 1995

[30] Foreign Application Priority Data

Feb. 5, 1994 [GB] United Kingdom ............ 9402235

[51] Int. Cl.$^6$ .................................................. A61F 5/00
[52] U.S. Cl. ........................... 602/58; 602/52; 602/54
[58] Field of Search ............................... 206/440, 441; 602/41-59; 128/888, 889

[56] References Cited

U.S. PATENT DOCUMENTS

| | | | |
|---|---|---|---|
| 3,285,245 | 11/1966 | Eldredge et al. | 602/57 X |
| 4,706,662 | 11/1987 | Thompson | 602/42 |
| 5,310,402 | 5/1994 | Rollband | 602/42 |

FOREIGN PATENT DOCUMENTS

| | | | |
|---|---|---|---|
| 340945 | 11/1989 | European Pat. Off. | 602/52 |

Primary Examiner—Richard J. Apley
Assistant Examiner—Kim M. Lee
Attorney, Agent, or Firm—Larson & Taylor

[57] ABSTRACT

A conformable material is described which comprises a backing layer having an adhesive layer on a first surface and a removable protector covering the adhesive layer and a removable carrier layer on the non-adhesive surface of the backing layer. The carrier layer and the protector layer are provided with slits substantially the length of the longitudinal or major axis.

10 Claims, 1 Drawing Sheet

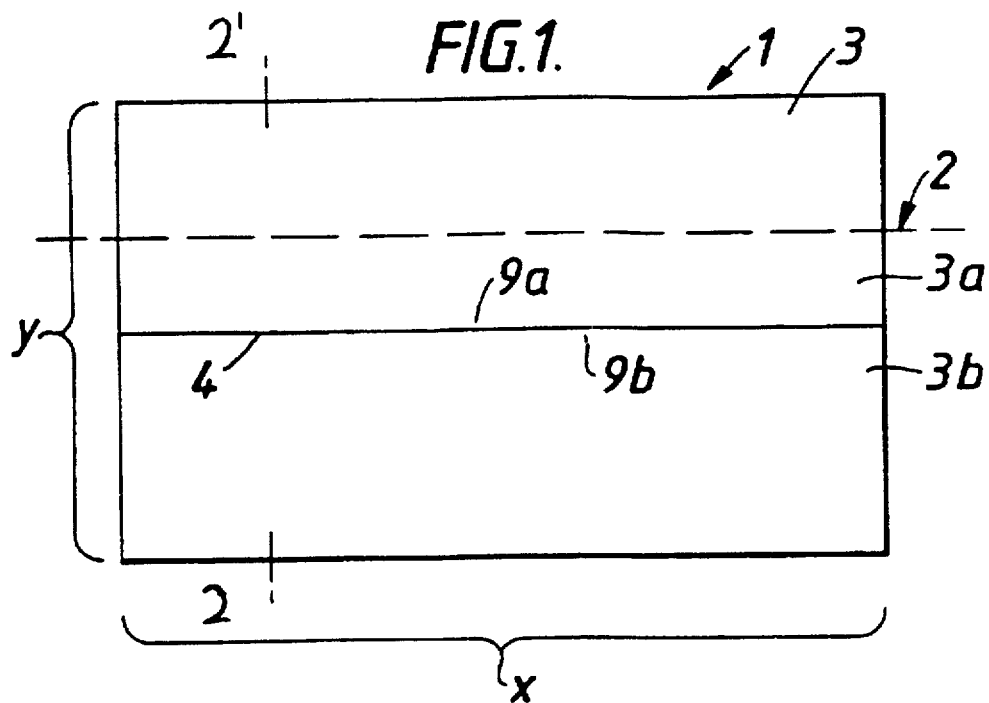
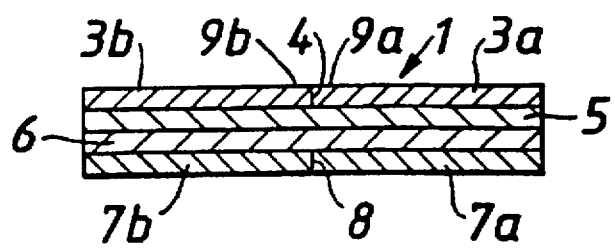
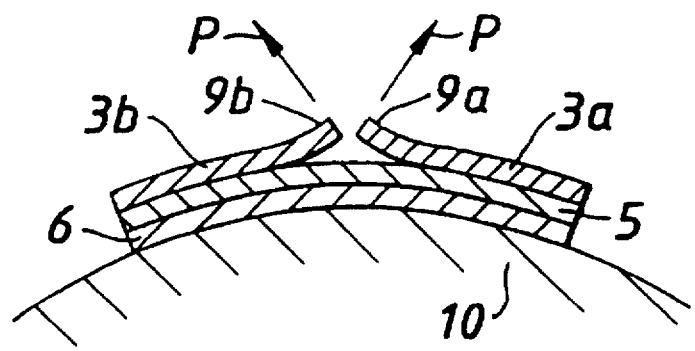

ADHESIVE MATERIAL WITH REMOVABLE CARRIER

The present invention relates to conformable materials such as wound dressings and adhesive tapes, eg. tapes for attaching non-adhesive dressings to a patients body; and to methods of making such conformable materials.

Conventional adhesive dressings comprise a backing layer, eg. a thin film layer, having an adhesive layer on one surface, a removable protector covering the adhesive layer and a carrier layer on the non-adhesive surface of the backing layer are known. Such dressings may be provided with a v-shaped handle to facilitate removal of the protector layer in particular. Such dressings include those available as OPSITE FLEXIGRID (Trade Mark) in the UK from Smith & Nephew Medical.

Flexible or conformable articles, such as adhesive medical tapes, surgical sheets, adhesive dressings and plasters provided with an adhesive surface covered by a protective paper film layer are known from British Patent Application No.2148125A which describes longitudinal flexible articles provided with a protective paper layer covering an adhesive layer wherein a sinusoidal penetrating slit is provided along the longitudinal axis of the protective paper layer. GB2148125 also acknowledges prior art wherein the penetrating slit is substantially straight and not sinusoidal.

However, generally, thin film flexible or conformable articles, as well as requiring a protector layer over the adhesive, require a carrier layer to facilitate handling of the film once the protector layer is removed. GB2148125 does not describe the use of such carrier layers and conventionally known carrier layers, such as those sold as OPSITE FLEXIGRID are not suitable for use in, eg. adhesive medical tapes which may be in roll form.

Carriers are employed in some adhesive dressings, as described in European Patent Applications 081990, 0340945 and 0168174. However the carriers are provided with v-shaped handles to facilitate removal of the carrier layer. European Patent application 0354315 describes an adhesive dressing with a carrier layer, with a cutting line to aid removal of the carrier layer.

The dressings described in the prior art are not suitable for use in a roll form as the lines for the removal of the carrier layer are perpendicular to the longitudinal axis of the dressing. This does not allow the flexibility of cutting a dressing size to suit and includes a more involved manufacturing process.

The object of the present invention is to provide a flexible material, eg. a dressing or tape material, which may optionally be in roll form and overcomes or mitigates the aforementioned problems.

According to the present invention there is provided a conformable material with a longitudinal axis which comprises a backing layer having an adhesive layer on a first surface and a removable protector covering the adhesive layer and a removable carrier layer on the non-adhesive surface of the backing layer characterised in that the carrier layer is provided with at least one slit substantially parallel to the longitudinal axis of the conformable material.

According to a further feature of the present invention there is provided a conformable material with a longitudinal axis which comprises a backing layer having an adhesive layer on a first surface and a removable protector covering the adhesive layer, the removable protector being provided with a slit substantially the length of one of its axes and a removable carrier layer on the non-adhesive surface of the backing layer characterised in that the carrier layer is provided with at least one slit substantially parallel to the longitudinal axis of the conformable material.

When the carrier layer is provided with a single slit then it comprises two release portions. It will be understood that the carrier layer may comprise more than two release portions. Thus for example the carrier layer may comprise three or four release portions.

When the carrier layer comprises three release portions, the carrier layer will be divided by two slits; when the carrier layer comprises four release portions, the carrier layer will be divided by three slits etc.

It is preferred that the carrier layer comprises two release portions, ie. a first and second release portion divided by a single slit. The slit may divide the carrier layer into two release portions of unequal dimensions. Preferably the slit divides the carrier layer into two release portions of substantially equal dimensions.

The slit in the carrier layer may be substantially straight or curved, a substantially straight slit is preferred. Where the slit is curved it will preferably have an axis of symmetry. If the conformable material possesses a longitudinal axis the axis of symmetry is preferably substantially parallel to the longitudinal axis of the conformable material.

When the protector layer is provided with a single slit then it comprises two release portions. The protector layer may comprise more than two release portions. Thus for example the protector layer may comprise three or four release portions. When the protector layer comprises three release portions, the protector layer will be divided by two slits; when the protector layer comprises four release portions, the protector layer will be divided by three slits etc.

It is preferred that the protector layer comprises two release portions, ie. a first and second release portion divided by a single slit. The slit may divide the protector layer into two release portions of unequal dimensions. Preferably the slit divides the protector layer into two release portions of equal dimensions.

The slit in the protector layer may be straight or curved, eg. such as that described in the prior art, a substantially straight slit is preferred. Where the slit is curved it will preferably have an axis of symmetry. If the conformable material possesses a longitudinal axis the axis of symmetry is preferably substantially parallel to the longitudinal axis of the conformable material.

Where the conformable material is, for example, an adhesive tape, such as a medical adhesive tape, ie. it has a longitudinal axis, the slit in the carrier layer or the protector layer preferably lies substantially along the longitudinal axis such as the slit in the protector layer described in GB2148125A. Such materials are particularly suited for use in a dispenser, for example, in roll form.

When the conformable material is provided with a slit in the carrier layer and the protector layer, the slits may be of the same or different shape and dimensions, for example one slit may be curved and the other substantially straight. It is preferred that both slits are substantially straight and both lie substantially parallel to the longitudinal axis of the material. Both slits may be the same or different distances from the edges of the conformable material. It is preferred that both slits are substantially equi-distant from the edges, eg. the longitudinal edges, of the conformable material.

The carrier layer may be any suitable conformable material which can be put in roll form. Thus suitable materials include, paper, foil or polymeric films. Preferably the carrier layer is a polymeric film.

Suitable polymeric films carrier layers are those disclosed in UK Patent No.2219211. The carrier layer may be opaque. Preferably the carrier layer is transparent. The carrier layer may be adhesively bonded to the backing layer using any suitable adhesive. The adhesive should have a peeling strength such that on removal of the carrier layer from the backing layer, the backing layer is not dislodged from the skin. Thus the peeling strength of the adhesive on the skin-facing surface of the backing layer should be greater than the peeling strength of the adhesive on the non-skin-facing surface of the backing layer. The carrier layer preferably comprises reference marks as disclosed in GB2219211. Thus for example, the reference marks may indicate dimensions, eg. 20 cm, 35 cm, etc.

In a preferred embodiment of the present invention, the conformable material comprises a carrier layer which is non-adhesively bonded to the backing layer. A suitable method of non-adhesively bonding the carrier layer to the backing layer is disclosed in GB2219211.

The carrier layer may have a greater surface area than the surface area of the backing layer. Thus the carrier layer may have one or more edge portions which extend beyond the backing layer. Where such edge portions are present they may be used as handles for gripping to aid removal of the carrier layer. Preferably the edges of the carrier layer are co-terminous with the edges of the backing layer.

The conformable material of the present invention may suitably be used as a wound dressing. Where the material is intended for use as a wound dressing it may preferably be provided in a sterile form. Where the conformable material is provided in sterile form it is advantageously provided in bacteria impervious pouches. Such packed forms can be prepared under aseptic conditions or alternatively sterilised after packing by a conventional procedure.

Alternatively the dressing may be provided in a non-sterile form, which is suitable for sterilisation using conventional sterilisation techniques such as steam sterilisation, ethylene oxide sterilisation or gamma irradiation.

Alternatively the conformable material may be used as an adhesive tape, eg. an adhesive medical tape. The tape may be sterile or non-sterile. Since one of the main functions of the tape of the present invention is to secure non-adhesive dressings to a subject, it will be understood that as the tape does not come into contact with the wound, it is not essential that it is sterile. Since sterilisation involves a further processing step and therefore adds to the expense of the process, it is preferable that the tape is non-sterile.

As the conformable material, whether it is to be used as a dressing or a tape, will in use, be in direct contact with the skin, it should preferably have a moisture vapour permeability of at least 300 $gm^{-2}$ 24 $hr^{-1}$ at 37.5° C. and at a relative humidity difference of 10 to 100%. It has been found that such moisture vapour transmission rates will prevent maceration of the skin.

The moisture vapour permeability (MVP) of the backing layer having an adhesive layer on its skin-facing surface, which will hereinafter be referred to as the adhesive coated backing layer, may be varied depending on the particular intended use of the conformable material. Thus, eg. it may be desired that the material have a low MVP. A low MVP may be achieved by either coating a backing layer of high MVP with a continuous layer of adhesive of low MVP with an adhesive which may be in the form of a continuous, microporous, screen-printed or pattern spread coating which may have a high or low MVP. Thus the skilled man would appreciate which adhesives and which polymer films could be combined to provide a backing layer having an adhesive layer on its skin-facing surface, of the correct MVP.

The moisture vapour transmission rates may be measured according to the method disclosed in WO91/01706.

The backing layer may comprise a polymeric film, a woven or a non-woven material. Where the backing layer is a polymeric film, it may be a discontinuous film. Preferably where the conformable material is for use as a wound dressing, the backing layer is continuous. Where the conformable material comprises a backing layer which is a woven or non-woven material, ie. discontinuous, and the material is desired for use as a wound dressing, it may comprise an additional continuous layer, eg. a continuous polymeric film, over the non-skin facing surface of the backing layer. Covering of the discontinuous backing layer in such a manner, provides a bacterial and a waterproof barrier. Alternatively where the backing layer is discontinuous, the bacterial barrier may be provided by providing a continuous adhesive layer on the first surface of the backing layer. A continuous adhesive layer may be formed by, eg. spreading or spraying a suitable adhesive onto the skin facing surface of the backing layer.

Suitable polymeric films for use as the backing layer include elastic or non-elastic, natural or synthetic polymers.

The backing layer may be opaque. Preferably the backing layer may be transparent to allow observation of the wound when the conformable material is on the skin.

Suitable backing layers can be of any of the thin transparent or translucent conformable backing film layers used on conventional adhesive dressings.

Preferred materials for forming the backing layer of the conformable materials are elastomeric moisture vapour transmitting films.

Suitably the backing layer may comprise any of those materials which are conventionally employed to form thin film surgical dressings. Suitable materials include those described in United Kingdom Patent No.1280631, European Patent Nos.51935, 91800 and 178740.

Favoured elastomeric moisture vapour transmitting films include those formed from polyether polyurethane, polyester polyurethane, hydrophilic polyurethane and polyester-polyether copolymers.

Suitable polyether polyurethanes are described in U.S. Pat. No. 2899411. Suitable polyester polyurethanes are described in U.S. Pat. No. 2871218. Apt polyester and polyether polyurethanes are known as ESTANE (Trade Mark) are available from B F Goodrich and in particular grades 5701, 5702, 5703, 5714F and 580201.

Other favoured materials include hydrophilic polymers such as hydrophilic polyurethanes, including those described in United Kingdom Patent No.2093190B, especially the polyurethane described in Example 2 therein.

Further suitable materials are disclosed in European Patent No.91800.

Other apt materials are elastomeric polyether polyesters, for example those known as HYTRELS (Trade Mark) and polyether polyamides, for example those known as PEBAXES (Trade Mark).

An apt polyester-polyether copolymer is known as HYTREL 4056 available from Dupont.

Suitably the backing layer is moisture vapour permeable and has a moisture vapour transmission rate, of at least 300 $gm^{-2}$ 24 $hr^{-1}$ at 37° C., and 100% to 10% relative humidity difference and 37.5° C., preferably at least 500 $gm^{-2}$ 24 $hr^{-1}$, more preferably at least 1200 $gm^{-2}$ 24 $hr^{-1}$ and especially at least 1600 $gm^{-2}$ 24 $hr^{-1}$.

The thickness of the films used for the backing layer may be from 9 to 100 µm and may suitable be from 9 to 80 µm. More suitably the backing layer is 15 to 50 µm thick and can preferably be 20 to 40 µm for example 27.5, 30 and 35 µm.

The adhesive used in the invention must be compatible with the skin. Suitable adhesives include synthetic polymers or mixtures thereof. Such adhesives may be selected from those described in British Patent Specification No.1280631 and European Patent Application NO.35399. Suitable adhesives are formed from acrylate ester copolymers or polyvinyl ethyl ethers. If desired such adhesives may incorporate an antibacterial agent.

A preferred pressure sensitive adhesive comprises a blend of high and low viscosity polyvinyl ethyl ethers. In particular adhesive composition A, disclosed in British Patent Specification No.1280631. Other preferred pressure sensitive adhesives comprise copolymers of acrylate ester with acrylic acid for example as disclosed in European Patent Application No.35399 and in particular a copolymer of 47 parts by weight of butyl acrylate, 47 parts by weight of 2-ethylhexyl acrylate and 6 parts by weight of acrylic acid with an intrinsic viscosity of at least 1.9 dl/g polymerised in acetone according to the general method given in the above European Application.

Suitably the adhesive is employed at a mass weight per unit area of 20 to 80 $gm^{-2}$, more suitably at 20 to 45 $gm^{-2}$ and preferably at 25 to 35 $gm^{-2}$, for example 29 $gm^{-2}$ or 32 $gm^{-2}$.

Suitably the adhesive layer is applied to the skin-facing surface of the backing layer as a continuous layer. Such adhesives which are applied continuously will have a moisture vapour permeability which is at least 300 $gm^{-2}$ 24 $hr^{-1}$ and more preferably at least 500 $gm^{-2}$ 24 $hr^{-1}$ when measured at 37° C. and 100% to 10% relative humidity.

Alternatively the adhesive layer may be in the form of a pattern spread or discontinuous spread adhesive layer using a conventional surgical adhesive prepared and spread by the method described in, eg. British Patent No.819635. The adhesive may also be in the form of a porous or microporous layer.

The dimensions of the conformable material of the present invention will vary depending on whether the material is for use as a wound dressing or as a tape as hereinbefore described. It will be clear that in both cases, the material comprises a longitudinal axis and a transverse axis. By definition the dimensions of the longitudinal axis (which is equal to the length of the conformable material) is greater than that of the transverse axis (which is equal to the width of the conformable material). Where the conformable material is for use as a wound dressing it will aptly have dimensions of from 1 cm×3 cm to 30 cm×40 cm for example, 2 cm×8 cm, 8 cm×12 cm, 10 cm×12 cm, 15 cm×20 cm, 20 cm×30cm, 25 cm×30 cm and 30 cm×40 cm. It is clear that the size of the dressing will be chosen depending upon the size of the wound upon which it is to be used for example the sizes 1 cm×3 cm and 8 cm×12 cm will be used on small wounds while the larger sizes are suitable for donor sites.

Where the conformable material is for use as a tape, the tape may be used for a wide range of purposes. Thus the tape may be used to secure a catheter in place or to secure a non-adhesive dressing, eg. a hydrocolloid dressing in place.

Where the conformable material is for use as a tape, the minimum dimensions of the tape will generally be dictated by the particular intended use as above discussed. Thus where the tape is to be used to attach a dressing to the subjects skin, the dimensions of the tape, ie. the length and the width thereof will be dictated by the dimensions of the dressing. Thus where the dressing has, eg. a length of 20 cm, it will be clear that where a single piece of tape is to be used, it will require a length greater than 20 cm to ensure an overlap at either end of the dressing. Clearly to attach the dressing securely to the skin the tape should be applied along each edge of the dressing. It will be understood that a plurality of pieces of tape, none of which has a length as long as the dressing to be secured, may alternatively be used.

In use, the protector layer is removed and the adhesive coated backing layer is adhered to the patients skin. The curved surface of the patients body causes the first and second portions of the carrier layer to lift away from the backing layer along the slit. As the portions of the carrier layer lift away, they may be easily removed from the backing layer by pulling gently.

In a further embodiment of the present invention the conformable material may be in roll-form. Thus as will hereinafter be described, the conformable material may be produced in lengths of any desired size. Thus, eg. a conformable material having an extended length of, eg. 3 m can be produced, this length being presented in a non-extended roll-form, the roll being unwound as desired and cut to the desired length.

The backing layer, the adhesive layer and the protector layer may be manufactured by any suitable method known to those skilled in the art. Thus one method of manufacture is to apply an adhesive layer to a suitable release layer protector and thereafter cast a synthetic polymer, eg. ESTANE onto the adhesive layer. Where desired, a carrier layer may then be applied to the backing layer by, eg. the method disclosed in UK Patent No.2219211.

To render the conformable material to the desired dimensions, the conformable material is passed by a transfer means under a set of rotating knives, the knives rotating about an axis of rotation perpendicular to the direction of movement of the conformable material. The transfer means may be a conventional conveyor belt. The set of rotating knives comprises at least two cutting knives which pass through the conformable material and a knife which passes through the carrier layer only, with which it comes into contact. The latter knife will hereinafter be referred to as the "crack-back" knife. Where there is one "crack-back" knife, it will be positioned intermediate the cutting knives. The distance between the cutting knives will determine the width of the conformable material, said distance being easily adjustable as desired. The crack-back knife may be positioned at any point intermediate the cutting knives. In a preferred embodiment the crack-back knife is equi-distant between the cutting knives. Where it is desired to produce a conformable material wherein there is a slit in the protector layer and the carrier layer, the conformable material is first passed along the transfer means with the carrier layer facing upwards and subsequently with the protector facing upwards.

Where the conformable material is required in the form of discrete lengths, an additional cutting knife may be placed above the means of transfer. The axis of rotation of said cutting knife being parallel to the direction of movement of the conformable material.

The conformable material of the invention will be illustrated by reference to the following figures.

FIG. 1 is a plan view of the conformable material in the form of a dressing, seen from the side of the carrier layer, FIG. 2 is a cross-sectional view in the plane of I–I' of FIG. 1, and FIG. 3 is a cross-sectional view of the material of FIG. 2 in use.

FIG. 1 shows the conformable material in the form of a dressing which comprises a longitudinal axis, illustrated by dotted line 2, the carrier layer 3 being provided with a slit to produce a first and second carrier portion 3a and 3b respectively with facing edges 9a and 9b. The dressing has a length x and a width y.

Referring to FIGS. 2 and 3. The carrier portions 3a and 3b cover a backing layer 5. An adhesive layer 6 on the skin facing surface is covered by protector layer portions 7a and 7b, which are divided by a slit 8. When the conformable material 1 is positioned on a patients skin 10 and adhered with adhesive layer 6, the contours of the patients skin 1 cause the edges 9a and 9b to lift away from the backing layer 5.

In use the edges 9a and 9b of the carrier layer portions 3a and 3b may be pulled, for example in direction to P, to remove them from the backing layer 5.

What is claimed is:

1. A conformable tape material having a longitudinal axis comprising a backing layer having an adhesive layer on a first surface and an opposed non-adhesive surface, a removable protector covering the adhesive layer, and a removable carrier layer removably bonded over the opposed non-adhesive surface of the backing layer characterized in that the carrier layer is provided with at least one slit substantially parallel to the longitudinal axis of the conformable material and that the removable protector is provided with at least one slit which is coaxial with a slit in the carrier layer.

2. A material according to claim 1, wherein the carrier layer comprises one slit.

3. A material according to claim 2, wherein the slit divides the carrier into two release portions of substantially equal dimensions.

4. A material according to claim 1, wherein each slit in the carrier layer is substantially straight.

5. A material according to claim 1, wherein the carrier layer is a polymeric film.

6. A material according to claim 1, wherein the backing layer has a moisture vapor permeability of at least 300 $gm^{-2}$ 24 $hr^{-1}$ at 37.5° C. and at a relative humidity difference of 10 to 100%.

7. A material according to claim 6 wherein the polymer film is a hydrophilic polyurethane.

8. A material according to claim 6 wherein the thickness of the backing layer is from 9 to 100 µm.

9. A material according to claim 1 wherein the pressure sensitive adhesive comprises a blend of high and low viscosity polyvinyl ethyl ethers.

10. A material according to claim 1 wherein the carrier layer is non-adhesively bonded to the backing layer.

* * * * *